(12) United States Patent
Lutz et al.

(10) Patent No.: US 8,784,910 B2
(45) Date of Patent: Jul. 22, 2014

(54) ANTIMICROBIAL COMPOSITIONS

(75) Inventors: Patrick Jay Lutz, Nazareth, PA (US);
Olga Borokhov, Chatham, NJ (US);
Abraham Shibu, Stewartsville, NJ (US)

(73) Assignee: Lonza Inc., Fair Lawn, NJ (US)

( * ) Notice: Subject to any disclaimer, the term of this patent is extended or adjusted under 35 U.S.C. 154(b) by 48 days.

(21) Appl. No.: 12/402,458

(22) Filed: Mar. 11, 2009

(65) Prior Publication Data

US 2009/0175966 A1    Jul. 9, 2009

Related U.S. Application Data

(63) Continuation of application No. 10/639,247, filed on Aug. 12, 2003, now abandoned.

(60) Provisional application No. 60/403,169, filed on Aug. 12, 2002, provisional application No. 60/403,004, filed on Aug. 12, 2002.

(51) Int. Cl.
*A01N 65/00* (2009.01)

(52) U.S. Cl.
USPC ........... 424/739; 424/725; 514/701; 510/119; 510/130

(58) Field of Classification Search
USPC ........... 424/739, 725, 735; 514/701; 510/119, 510/130
See application file for complete search history.

(56) References Cited

U.S. PATENT DOCUMENTS

| | | | |
|---|---|---|---|
| 4,469,674 A | 9/1984 | Shah et al. | |
| 4,477,361 A | 10/1984 | Sperti et al. | |
| 4,525,480 A | 6/1985 | Berke et al. | |
| 4,920,158 A * | 4/1990 | Murray et al. | 523/111 |
| 5,149,715 A | 9/1992 | Armstrong et al. | |
| 5,294,456 A | 3/1994 | Jenkins et al. | |
| 5,306,707 A | 4/1994 | Burrell et al. | |
| 5,336,500 A | 8/1994 | Richter | |
| 5,484,816 A | 1/1996 | Yanagida et al. | |
| 5,536,501 A | 7/1996 | Emerson et al. | |
| 5,540,853 A | 7/1996 | Trinh et al. | |
| 5,657,574 A | 8/1997 | Kandathil et al. | |
| 5,658,584 A | 8/1997 | Yamaguchi et al. | |
| 5,676,958 A | 10/1997 | Emerson et al. | |
| 5,738,861 A | 4/1998 | Emerson et al. | |
| 5,839,224 A | 11/1998 | Emerson et al. | |
| 5,965,518 A | 10/1999 | Nakatsu et al. | |
| 6,042,861 A | 3/2000 | Anslow et al. | |
| 6,350,784 B1 | 2/2002 | Squires | |
| 6,383,534 B1 * | 5/2002 | Dyrr et al. | 426/74 |
| 6,559,110 B1 | 5/2003 | Lopes | |
| 2001/0055646 A1 | 12/2001 | Blyth et al. | |
| 2002/0001582 A1 | 1/2002 | Charter et al. | |
| 2002/0028280 A1 * | 3/2002 | Yamaguchi et al. | 426/590 |
| 2002/0039981 A1 | 4/2002 | Lopes | |
| 2003/0017215 A1 | 1/2003 | Bessette et al. | |
| 2003/0017218 A1 | 1/2003 | Bessette et al. | |

FOREIGN PATENT DOCUMENTS

| | | |
|---|---|---|
| EP | 0 570 794 A2 | 12/1984 |
| WO | WO-84/04886 | 12/1984 |
| WO | WO-99/21433 | 5/1999 |
| WO | WO99/66793 | * 12/1999 |
| WO | WO-00/69279 | 11/2000 |
| WO | WO-01/87095 | 11/2001 |

OTHER PUBLICATIONS

Besser et al., An Outbreak fo Diarrhea and Hemolytic Uremic Syndrome From *Escherichia coli* 0157:H7 in Fresh-Pressed Apple Cider, JAMA, vol. 269 No. 17 May 5, 1993 pp. 2217-2220.*
Pocker et al. Hydrolysis of D-Glucono-&lactone. I. General Acid-Base Catalysis, Solvent Deuterium Isotope Effects, and Transition State Characterization, Journal of the American Chemical Society 95:I / Jan. 10, 1973.*
International Search Report for PCT/US03/25090.
European Search Report for EP 2387882 A2 published Oct. 31, 2012.

* cited by examiner

*Primary Examiner* — Jason Sims
*Assistant Examiner* — Ibrahim D Bori
(74) *Attorney, Agent, or Firm* — Hoffmann & Baron, LLP

(57) ABSTRACT

The present invention provides an antimicrobial composition comprising an antimicrobial effective amount (such as a preservative, bactericidal, and/or fungicidal effective amount) of a mixture comprising at least two of:
  (a) lemon grass oil;
  (b) cinnamaldehyde, cinnamon oil, *Cinnamomum cassia*, cinnamon extract, *cassia* leaf oil, 3,4-dihydroxycinnamic acid or salt thereof, or a mixture thereof;
  (c) sorbic acid, or a salt thereof;
  (d) erythorbic acid, or a salt thereof;
  (e) benzoic acid, or a salt thereof;
  (f) arabinogalactan, galactoarabinan, or a mixture thereof;
  (g) a hexahydro-iso-alpha-acid, tetrahydro-iso-alpha-acid, or a mixture thereof;
  (h) *Achillea fragrantissima* (*Santolina fragrantissima* Forssk., lavender cotton) oil; and
  (i) δ-gluconolactone.

The present invention also provides a product (preferably a product other than a foodstuff, pharmaceutical, or cosmetic) comprising a preservative effective amount of cinnamaldehyde or a mixture of cinnamaldehyde and one or more alkanol-dialkyl hydantoins.

12 Claims, 7 Drawing Sheets

% stability based on Bacteria count at Day 21 of test - >$10^5$ organisms in formulation gives less than 10% stability, $10^3$ - $10^4$ organisms in formulation gives <50% stability, $10^2$ - $10^1$ organisms gives >80% stability, and ,<10 organisms gives 100% stability.

% stability based on Bacteria count at Day 14 of test - >$10^5$ organisms in formulation gives less than 10% stability, $10^3$-$10^4$ organisms in formulation gives <50% stability, $10^2$ - $10^1$ organisms gives >80% stability, and ,<10 organisms gives 100% stability.

% stability based on Fungal count at Day 7 of test - >$10^4$ organisms in formulation gives less than 10% stability, $10^2$-$10^3$ organisms in formulation gives <50% stability, >10 organisms gives 80% stability, and <10 organisms gives 100% stability.

% stability based on Fungal count at Day 14 of test - >10⁴ organisms in formulation gives less than 10% stability, 10²-10³ organisms in formulation gives <50% stability, >10 organisms gives 80% stability, and <10 organisms gives 100% stability.

% stability based on Fungal count at Day 7 of test - >10⁴ organisms in formulation gives less than 10% stability, 10²-10³ organisms in formulation gives <50% stability, >10 organisms gives 80% stability, and <10 organisms gives 100% stability.

% stability based on Fungal count at Day 7 of test - >10⁴ organisms in formulation gives less than 10% stability, $10^2$-$10^3$ organisms in formulation gives <50% stability, >10 organisms gives 80% stability, and <10 organisms gives 100% stability.

ANTIMICROBIAL COMPOSITIONS

This application is a continuation of U.S. application Ser. No. 10/639,247, filed Aug. 12, 2003, which claims the benefit of prior U.S. Provisional Application No. 60/403,004, filed Aug. 12, 2002, and prior U.S. Provisional Application No. 60/403,169, filed Aug. 12, 2002, and the disclosures of each are herein incorporated by reference.

FIELD OF THE INVENTION

The present invention relates to (1) antimicrobial compositions, (2) methods of killing and/or inhibiting the growth or microorganisms, (3) preserving products with the same, and (4) methods of potentiating antimicrobial compositions.

BACKGROUND OF THE INVENTION

Natural products, while often safe, are generally expensive and do not have biocidal efficacy against a broad spectrum of organisms such as gram negative and positive bacteria and fungi. Most natural products are only effective against gram positive bacteria at relatively high concentrations and are not effective against gram negative bacteria or fungi.

Cinnamaldehyde is a natural product which has been used (1) as a flavoring agent, (2) in preservative systems, and (3) to control insect and arachnid populations. See U.S. Pat. Nos. 4,525,480, 5,306,707, 5,536,501, 5,676,958, and 5,839,224.

There is a continuing need for low cost and safe preservative systems which are effective against a broad spectrum of microorganisms.

SUMMARY OF THE INVENTION

The present invention provides an antimicrobial composition comprising an antimicrobial effective amount (such as a preservative, bactericidal, and/or fungicidal effective amount) of a mixture comprising at least two of:

(a) lemon grass oil;

(b) cinnamaldehyde, cinnamon oil, *Cinnamomum cassia*, cinnamon extract, *cassia* leaf oil, 3,4-dihydroxycinnamic acid or salt thereof, or a mixture thereof;

(c) sorbic acid, or a salt thereof;

(d) erythorbic acid, or a salt thereof;

(e) benzoic acid, or a salt thereof;

(f) arabinogalactan, galactoarabinan, or a mixture thereof;

(g) a hexahydro-iso-alpha-acid, tetrahydro-iso-alpha-acid, or a mixture thereof;

(h) *Achillea fragrantissima* (*Santolina fragrantissima* Forssk., lavender cotton) oil; and (i) δ-gluconolactone.

Preferably the mixtures of the present invention include an antimicrobial (e.g., preservative, bactericidal, and/or fungicidal) synergistic effective amount of the aforementioned ingredients.

Preferred mixtures of the present invention include, but are not limited to, those shown in the table below.

| Mixture No. | Component (a) | Component (b) | Component (c) |
|---|---|---|---|
| 1 | cinnamaldehyde, lemon grass oil, arabinogalactan, galactoarabinan, or a mixture thereof | sorbic acid or a salt thereof | — |
| 2 | cinnamaldehyde | *achillea* oil, arabinogalactan, galactoarabinan, or a mixture thereof | — |
| 3 | cinnamaldehyde | arabinogalactan, galactoarabinan, or a mixture thereof | sorbic acid or salt thereof |
| 4 | cinnamaldehyde | sorbic acid or a salt thereof | — |
| 5 | cinnamaldehyde | erythorbic acid or a salt thereof | — |
| 6 | benzoic acid or a salt thereof (e.g., sodium benzoate) | erythorbic acid or a salt thereof | — |
| 7 | sorbic acid or a salt thereof | erythorbic acid or a salt thereof | — |
| 8 | cinnamaldehyde, benzoic acid or a salt thereof (e.g., sodium benzoate), or sorbic acid or a salt thereof | δ-gluconolactone | — |

In all of the aforementioned mixtures containing erythorbic acid (or salt thereof) or δ-gluconolactone, the erythorbic acid (or salt thereof) or δ-gluconolactone potentiates the antimicrobial efficacy of the preservative (e.g., sorbic acid or benzoic acid) in the mixture.

Another embodiment is a method of killing and/or inhibiting the growth of microorganisms on a substrate or in or on a product by applying an effective amount of the antimicrobial composition of the present invention to the substrate or the product.

Another embodiment is a method for potentiating the antimicrobial efficacy of an antimicrobial composition containing sorbic acid, benzoic acid, or salts thereof, by adding or including erythorbic acid or a salt thereof, or δ-gluconolactone in the antimicrobial composition.

Yet another embodiment is a product comprising an antimicrobial, preservative, bactericidal, and/or fungicidal effective amount of the antimicrobial composition of the present invention. The product may be a solid or liquid. The antimicrobial compositions of the present invention are particularly effective as preservatives for personal care products.

Yet another embodiment is a method of preserving a product (e.g., a personal care product) by incorporating a preservative effective amount of the antimicrobial composition of the present invention into the product.

Yet another embodiment is a method of killing and/or inhibiting the growth of tree or other plant fungus on a plant (such as a tree) by applying an effective amount of the antimicrobial composition of the present invention to the plant and/or the soil surrounding the plant.

Yet another embodiment is a product (preferably a product other than a foodstuff, pharmaceutical, or cosmetic) comprising a preservative effective amount of cinnamaldehyde or erythorbic acid or a salt thereof (e.g., sodium erythorbate). The product is generally substantially free or completely free of parabens (such as methylparaben, ethylparaben, and propylparaben). The product may be, for example, a household (e.g., personal care), industrial, or institutional product. Preferred personal care products include, but are not limited to, shampoos, lotions (e.g., body lotions), conditioners, and soaps. Suitable household products include, but are not limited to, fabric softeners, laundry detergents, and hard surface cleaners. According to one embodiment, the product contains less than about 1, 0.5, 0.4, 0.3, 0.25, 0.2, 0.15, 0.1, 0.09, 0.08, 0.07, 0.06, 0.05, 0.04, 0.03, 0.02, or 0.01% by weight of parabens, based upon 100% total weight of product. According to one preferred embodiment, the product contains less than a smelling effective amount of cinnamaldehyde. The product preferably contains more than 0.01, 0.03, 0.05, 0.07, 0.09, or 0.1% by weight of cinnamaldehyde. The product is preferably substantially free or completely free of cinnamon oil. According to one embodiment, the product does not contain a preservative effective amount of a preservative other than cinnamaldehyde or erythorbic acid or a salt thereof. According to another embodiment, the only preservative in the product is cinnamaldehyde or erythorbic acid or a salt thereof.

Yet another embodiment is a method of killing and/or inhibiting the growth of microorganisms in or on a product (such as a product other than a foodstuff, pharmaceutical, or cosmetic) comprising applying an effective amount of cinnamaldehyde to the product. The product is preferably substantially free or completely free of parabens.

Yet another embodiment is a method of preserving a product (preferably a product other than a foodstuff, pharmaceutical, or cosmetic) comprising applying an effective amount of cinnamaldehyde to the product. The product may be substantially free or completely free of parabens.

Yet another embodiment is a method of killing and/or inhibiting the growth of microorganisms in or on a product (such as (i) a product other than a foodstuff or (ii) a product other than a foodstuff, pharmaceutical, or cosmetic) comprising applying an effective amount of erythorbic acid or a salt thereof to the product.

Yet another embodiment is a method of preserving a product (preferably (i) a product other than a foodstuff or (ii) a product other than a foodstuff, pharmaceutical, or cosmetic) comprising applying an effective amount of erythorbic acid or a salt thereof to the product. The product may be substantially free or completely free of parabens.

Yet another embodiment of the present invention is a method of killing and/or for inhibiting the growth of microorganisms on a substrate by applying an antimicrobial or preservative effective amount of cinnamaldehyde or erythorbic acid or a salt thereof (preferably without applying any parabens).

Yet another embodiment is a preservative formulation comprising an antimicrobial synergistic mixture comprising cinnamaldehyde and at least one conventional personal care preservative, such as isothiazolinones, benzisothiazolinones, and/or formaldehyde donors, such as alkanol substituted dialkylhydantoins. Preferably, the alkanol substituted dialkyl hydantoin is a compound of formula:

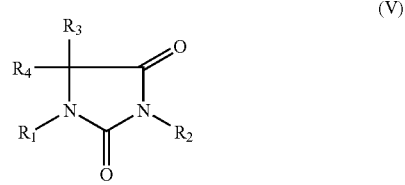

(V)

wherein $R_1$ and $R_2$ are each independently hydrogen or $(CH_2)OH$, with the proviso that both $R_1$ and $R_2$ cannot be hydrogen, and $R_3$ and $R_4$ are each independently methyl, ethyl, propyl, or aryl. Preferred alkanol substituted dialkylhydantoins include, but are not limited to, 1,3-dimethylol-5,5-dimethylhydantoin (DMDMH) and monomethylol dimethylhydantoin (MMDMH). Preferably, the preservative formulation comprises a preservative effective amount of the synergistic mixture. According to one embodiment, the preservative formulation comprises a batericidally and/or fungicidally effective amount of the synergistic mixture. The preservative formulation may contain less than a smelling effective amount of cinnamaldehyde. Preferably, the preservative formulation is substantially free or completely free of parabens. The preservative formulation may be incorporated into a product, such as those discussed in this application.

Yet another embodiment is a method of killing and/or inhibiting the growth of microorganisms in or on a product (such as a product other than a foodstuff, pharmaceutical, or cosmetic) comprising applying an effective amount of the aforementioned preservative formulation to the product. According to one embodiment, the product is substantially free or completely free of parabens.

Yet another embodiment of the present invention is a method of killing and/or for inhibiting the growth of microorganisms on a substrate by applying an antimicrobial or preserving effective amount of the preservative formulation of the present invention.

Yet another embodiment is a method of killing and/or inhibiting the growth of fungi on a substrate comprising applying an effective amount of the aforementioned preservative formulation to the product. According to one embodiment, the product is substantially free or completely free of parabens.

The formulations and products of the present invention preferably have a pH less than 10, 9, 8.5, or 8.

DETAILED DESCRIPTION OF THE INVENTION

Definitions

Figure 1:
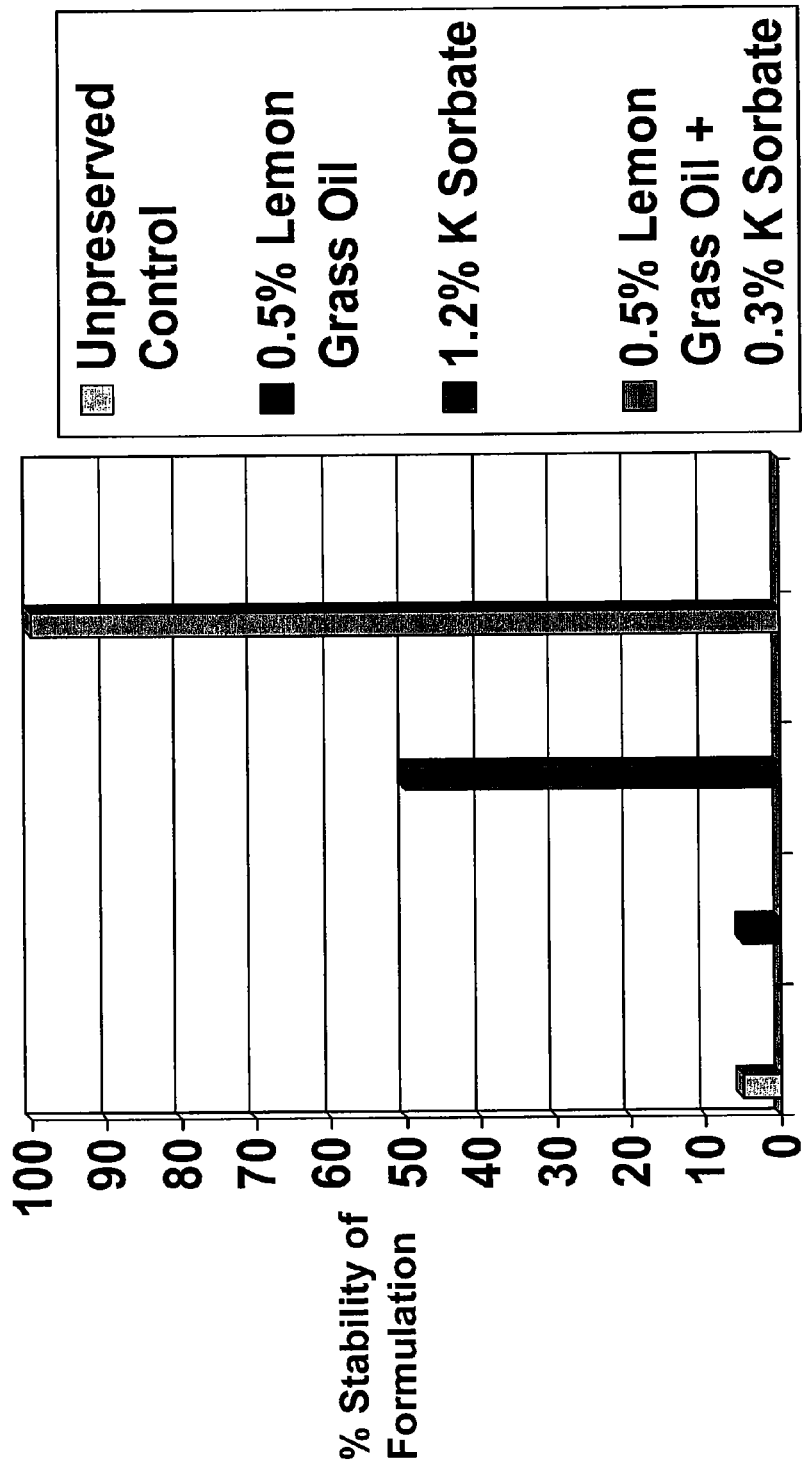
FIG. 1 is a bar graph of the stability of (a) an unpreserved shampoo, (b) a shampoo containing 0.5% (w/w) lemon grass oil, (c) a shampoo containing 1.2% (w/w) potassium sorbate, and (d) a shampoo containing 0.5% (w/w) lemon grass oil and 0.3% (w/w) potassium sorbate after 21 days (based on bacterial count).

The term "microorganisms" includes, but is not limited to, bacteria, fungi, yeasts, algae, insects, and pests.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "personal care products" refers to products intended for application to the human body, such as to skin, hair, and nails, including, but not limited to, shampoos, conditioners, creams, lotions (such as body lotions), cosmetics, and soaps.

The term "smelling effective amount" refers to a sufficient amount of an agent incorporated into a product to give the product an odor.

The term "potentiating" refers to the ability of a compound or composition to enhance or increase the effect of an antimicrobial compound or composition. Preferably, the efficacy of the combined mixture is greater than the additive effect of the ingredients.

Suitable salts of sorbic acid, erythorbic acid, and benzoic acid include, but are not limited to, alkali metal or alkali earth metal salts, such as potassium and sodium.

Components for Mixtures

Cinnamaldehyde from any source may be used in the present invention. For example, the cinnamaldehyde may be derived from cinnamon bark extracts (such as from bark and leaf), *cassia* leaf oil, *Cinnamomum cassia*, cinnamon oils, cinnamal, cinnamyl alcohol, and mixtures thereof.

A preferred salt of sorbic acid is potassium sorbate.

A preferred salt of erythorbic acid is sodium erythorbate.

A preferred salt of benzoic acid is sodium benzoate.

Arabinogalactan and galactoarabinan may be derived from Larex trees. Arabinogalactan is available as Larex UF™ from Larex Inc. of White Bear Lake, Minn.

Preferred hexahydro-iso-alpha-acids and tetrahydro-iso-alpha-acids are those obtained from hops extracts, such as Hexahop Gold™ (also referred to as Hexahop herein) available from John I. Haas, Inc. of Washington, D.C.

According to a specific embodiment, the antimicrobial composition contains at least 0.1% of sorbic acid, or a salt thereof, such as potassium sorbate.

Examples of Preferred Mixtures (i) Cinnamaldehyde and Sorbic Acids Erythorbic Acid, or a Salt Thereof A preferred mixture is cinnamaldehyde and sorbic acid or a salt thereof, such as potassium sorbate. Another preferred mixture is cinnamaldehyde and erythorbic acid or a salt thereof, such as sodium erythorbate. The weight ratio of cinnamaldehyde to (i) sorbic acid or a salt thereof or (ii) erythorbic acid or a salt thereof is preferably from about 10:1 to about 0.1:1 and more preferably from about 5:1 to about 0.2:1.

Concentrates of the mixture preferably include from about 2 to about 40% by weight of cinnamaldehyde and from about 10 to about 60% by weight of sorbic acid, erythorbic acid, or a salt thereof, in water, with or without a hydroxyl co-solvent (such as glycerin or ethanol, which increase the solubility and stability of the cinnamaldehyde in the blends).

Preferably, the pH of formulations including a mixture of (i) cinnamaldehyde and (ii) sorbic acid, erythorbic, or a salt thereof is less than 10, 9, 8.5, or 8. At a pH of less than 9, such formulations exhibit improved color stability. According to one preferred embodiment, the pH of a formulation containing a mixture of cinnamaldehyde and sorbic acid, erythorbic acid, or a salt thereof is lowered with hydrochloric acid. Preferably, a sufficient amount of hydrochloric acid is included in the formulation to lower its pH to less than 9, 8.5, or 8.

A preferred preservative formulation includes from about 5 to about 20% (w/w) cinnamaldehyde, from about 20 to 50% potassium sorbate, ethanol, and water. A more preferred preservative formulation includes about 15% cinnamaldehyde, about 40% potassium sorbate, 10% ethanol, and 35% water.

(ii) Combinations of Erythorbic Acid or a Salt Thereof, Citric Acid or a Salt Thereof, δ-Gluconolactone, Benzoic Acid or a Salt Thereof, Sorbic Acid, EDTA, or a Salt Thereof Another preferred mixture is (a) erythorbic acid or a salt thereof (e.g., sodium erythorbate) and (b) one or more of (i) citric acid or a salt thereof, (ii) δ-gluconolactone, (iii) benzoic acid or a salt thereof (e.g., sodium benzoate), (iv) sorbic acid or a salt thereof, or (v) ethylenediaminetetraacetic acid (EDTA) or a salt thereof.

Another preferred mixture is (a) benzoic acid or a salt thereof (e.g., sodium benzoate) and (b) one or more of (i) citric acid or a salt thereof, (ii) δ-gluconolactone, (iii) sorbic acid or a salt thereof, or (iv) ethylenediaminetetraacetic acid (EDTA) or a salt thereof.

Erythorbic acid and salts thereof typically are not color stable in formulations, such as shampoos. Surprisingly, it has been found that these mixtures are color stable. It has also been surprisingly found that erythorbic acid and salts thereof and δ-gluconolactone potentiate the biocidal efficacy of citric acid, benzoic acid, EDTA, and salts thereof.

Preferred mixtures include, but are not limited to, those in the table below. Preferred and more preferred weight ratios are also provided in the table.

| Mixture No. | Component (a) | Component (b) | Preferred Weight Ratio | More Preferred Weight Ratio |
|---|---|---|---|---|
| 1 | Benzoic Acid or a Salt Thereof | Erythorbic Acid or a Salt Thereof | about 0.1:1 to about 20:1 | about 0.2:1 to about 5:1 |
| 2 | Sorbic Acid or a Salt Thereof | Erythorbic Acid or a Salt Thereof | about 0.1:1 to about 20:1 | about 0.2:1 to about 5:1 |
| 3 | Benzoic Acid or a Salt Thereof | δ-gluconolactone | about 0.1:1 to about 20:1 | about 0.2:1 to about 5:1 |
| 4 | δ-gluconolactone | Erythorbic Acid or a Salt Thereof | about 0.1:1 to about 20:1 | about 0.2:1 to about 5:1 |
| 5 | δ-gluconolactone | Benzoic Acid or a Salt Thereof | about 0.1:1 to about 20:1 | about 0.2:1 to about 5:1 |

More preferred mixtures include, but are not limited to, those shown in the table below.

| Mixture No. | Component (a) | Component (b) | Preferred Weight Ratio | More Preferred Weight Ratio |
|---|---|---|---|---|
| 1 | Sodium Benzoate | Sodium Erythorbate | about 1:1 to about 5:1 | about 3:1 |
| 2 | Potassium Sorbate | Sodium Erythorbate | about 1:1 to about 5:1 | about 3:1 |
| 3 | Sodium Benzoate | δ-gluconolactone | about 1:1 to about 5:1 | about 3:1 |
| 4 | δ-gluconolactone | Sodium Erythorbate | about 1:1 to about 5:1 | about 3:1 |
| 5 | δ-gluconolactone | Sodium Benzoate | about 1:1 to about 5:1 | about 3:1 |

Antimicrobial Compositions

The antimicrobial compositions of the present invention are useful as antimicrobial, fungicidal, and bactericidal agents (such as against allergens, tree and plant fungi, and plant and tree bacteria) and as preservatives in the papermaking, textile, agricultural, and coating industries and in personal care, household, industrial, and institutional products. The antimicrobial composition may be incorporated into substrates susceptible to microbial growth to preserve them. For example, the preservative system may be incorporated into or be a personal care product, such as a shampoo, conditioner, cream, lotion (such as body lotion), cosmetic, or soap; a household product, such as a fabric softener, laundry detergent, or hard surface cleaner; or an industrial product, such as paint, coatings, wood, textile, adhesive, sealant, leather, rope, paper, pulp, paper board, sheet rock, ceiling tiles, plastic, fuel, petroleum, oil, rubber working fluid, metal working fluid, starches (such as pet food starch), or mineral slurry, such as a slurry of clay, calcium carbonate, or titanium oxide ($TiO_2$).

Generally, the product contains an antimicrobial, preservative, bactericidal, and/or fungicidal effective amount of the antimicrobial composition. According to one embodiment, the product contains from about 0.01 to about 2.0% by weight of each component of the antimicrobial composition, based upon 100% total weight of product. According to another embodiment, the product includes from about 0.1 to about 1 or 2% by weight of the antimicrobial composition, based upon 100% weight of total product.

Cinnamaldehyde Preservative Systems

Cinnamaldehyde and mixtures of (i) cinnamaldehyde and (ii) at least one of an alkanol dialkyl hydantoin, isothiazolone, and benzisothiazolinone (hereinafter referred to as "the preservative system") are useful as antimicrobial, fungicidal, and bactericidal agents (such as against allergens, tree and plant fungi, and tree bacteria) and as preservatives in the papermaking, textile, agricultural, and coating industries and in personal care, household, industrial, and institutional products. The preservative system may be incorporated into substrates susceptible to microbial growth to preserve them. For example, the preservative system may be incorporated into or be a personal care product, such as a shampoo, conditioner, cream, lotion (such as body lotion), cosmetic, or soap; a household product, such as a fabric softener, laundry detergent, or hard surface cleaner; or an industrial product, such as paint, coatings, wood, textile, adhesive, sealant, leather, rope, paper, pulp, paper board, sheet rock, ceiling tiles, plastic, fuel, petroleum, oil, rubber working fluid, metal working fluid, starches (such as pet food starch), or mineral slurry, such as a slurry of clay, calcium carbonate, or titanium oxide ($TiO_3$).

Generally, the antimicrobial composition and preservative system of the present invention acts quickly (e.g., reduces the microorganism (e.g., bacteria and/or fungi) count by 95, 99, 99.9, or 99.99% typically within an hour) and maintains efficacy (e.g., maintains less than 10 cfu/g) over long periods of time (e.g., for at least 7, 10, 14, or 28 days). The term "preservative effective amount" refers to an amount of the preservative system which maintains the microorganism count below 1000, 100, or 10 cfu/g for at least 1, 4, 7, 10, 14, or 28 days.

The antimicrobial composition and preservative system may include a solvent, such as water and water miscible solvents, including, but not limited to, alcohols (e.g., methanol, ethanol, propanol, iso-propanol, and butanol), glycols (e.g. glycerin, diglycerin, butylene glycol, butoxydiglycol, propylene glycol, and dipropylene glycol), esters, ethers, polyethers, and any combination of any of the foregoing. For example, the solvent may comprise water and one or more glycol and/or one or more alcohol, such as glycerin, phenoxyethanol, benzyl alcohol, or ethanol. A specific solvent system comprises water and a glycol, such as glycerin. A second specific solvent system comprises water and an alcohol, such as ethanol.

Other adjuvants may be included in the antimicrobial composition and preservative system as known to one of ordinary skill in the art. Suitable adjuvants include, but are not limited to, preservatives; solubilizing agents; chelating agents, such as ethylenediaminetetraacetic acid (EDTA) and salts thereof and zeolites; surfactants, such as cationic, anionic, nonionic, and amphoteric surfactants; antioxidants, such as butylated hydroxyanisole (BHA) and butylhydroxytoluene (BHT); amine oxides; tertiary amines; zinc compounds; hydrotropes; fluoride compounds; magnesium salts; calcium salts; carboxylic acids; phosphates; phosphonates; formaldehyde donors; glycereth-7; myristyl myristate; glutaraldehydes; biguanides; natural products, such as geranoil, usnic acid, and tea tree oils; and any combination of any of the foregoing. Suitable preservatives include, but are not limited to, quaternary ammonium chlorides; quaternary ammonium carbonates; benzalkonium chloride; iodine containing compounds, such as 3-iodo-2-propynyl butyl carbamate (IPBC); hydantoins, such as dimethylhydantoin and halogenated hydantoins; isothiazolinones; parabens, such as methylparaben, ethylparaben, and propylparaben; dehydroacetic acid and salts thereof; isocil; chloroxylenol; chlorhexidine; phenoxyethanol; benzyl alcohol; phenethyl alcohol; benzoic acid and salts thereof such as sodium benzoate; chlorobutanol; sorbic acid and salts thereof; triclosan; triclocarban; and any combination of any of the foregoing.

The antimicrobial composition and preservative system may be incorporated into an aqueous or oil based system or an emulsion. A suitable solvent for an oil based system is phenoxyethanol and/or benzyl alcohol.

The antimicrobial composition can be a liquid or a solid.

When the synergistic mixture contains only two ingredients from the list above, the weight ratio of the first component to the second component typically ranges from about 0.01:100 to about 100:0.01, preferably ranges from about 0.1:20 to about 20:0.1, and more preferably ranges from about 1:10 to about 10:1. When the synergistic mixture contains three components, the third component can be in any amount, but typically the weight ratio of the third component to either of the first two components is from about 0.01:100 to about 100:0.01.

To prepare a formulation containing the product of the present invention, a concentrate of the antimicrobial composition and preservative system is generally first prepared. The concentrate may include from about 0.01 to about 100% by weight of the antimicrobial composition and preservative system and preferably contains from about 5 to about 80% by weight of the antimicrobial composition, based upon 100% total weight of concentrate. For a two-component antimicrobial composition, the concentrate broadly contains from about 0.01 to about 99.99% by weight of the first component and from about 99.99% to about 0.01% by weight of the second component (based upon 100% total weight of concentrate). When the preservatives system is cinnamaldehyde, the concentrate may include from about 0.01 to about 100% cinnamaldehyde by weight and preferably contains from about 5 to about 80% cinnamaldehyde by weight, based upon 100% total weight of concentrate. Table A illustrates the components and the ranges of components present in a typical concentrate for the cinnamaldehyde/alkanol substituted dialkylhydantoin mixtures (based upon 100% total weight of concentrate).

TABLE A

| Ranges | Cinnamaldehyde | Alkanol Substituted Dialkylhydantoin, Isothiazolinone, Benzisothiazolinone |
|---|---|---|
| Broad | from about 0.01 to about 99.99% | from about 99.99 to about 0.01% |
| Preferred | from about 5 to about 95% | from about 95 to about 5% |

Before use, the concentrate is diluted, preferably with the same solvent as was used in the concentrate, and/or incorporated into a product. Use dilutions of the composition typically comprise an antimicrobial, preservative, fungicidally, or bactericidally effective amount of the antimicrobial composition or preservative system.

Generally, use dilutions contain from about 0.0001% or 0.01% to about 2% by weight of the concentrate. According to one preferred embodiment, use dilutions contain from about 0.1 to about 1% by weight of the concentrate. In more preferred embodiments, the use dilution contains 0.2, 0.25 or 0.30% by weight of the concentrate. The use dilution generally contains from about 0.01, to about 2.0% by weight of each antimicrobial ingredient, based upon 100% total weight of use dilution. According to a preferred embodiment, the antimicrobial composition contains from about 0.001 to about 10%, preferably from about 0.01 to about 1%, and more preferably from about 0.05 to about 0.5% by weight of each antimicrobial ingredient (e.g., cinnamaldehyde). When the preservative system is cinnamaldehyde, the use dilution may contain from about 0.001, 0.005, 0.01, 0.02, 0.03, 0.04, 0.05, 0.06, 0.07, 0.08, 0.09, or 0.1% to about 1, 0.5, 0.4, 0.3, 0.25, 0.2, 0.15, 0.1, 0.09, 0.08, 0.07, 0.06, 0.05, 0.04, 0.03, 0.02, or 0.01% by weight based upon 100% total weight of use dilution. Table B illustrates the components and generally the ranges of components present in the use dilution (based upon 100% total weight of use dilution).

TABLE B

| Ranges | Cinnamaldehyde | Alkanol Substituted Dialkylhydantoin, Isothiazolinone, Benzisothiazolinone |
|---|---|---|
| Broad | from about 0.001 to about 10% | from about 0.001 to about 10% |
| Preferred | from about 0.01 to about 1% | from about 0.01 to about 1% |
| More Preferred | from about 0.05 to about 0.5% | from about 0.05 to about 0.5% |

According to another embodiment, the aforementioned preservative system is incorporated into a product at a concentration of about 0.1 to about 1 or 2% by weight, based upon 100% total weight of product.

Another embodiment of the present invention is a method for inhibiting the growth of microorganisms, bacteria (e.g., *S. aureus* (ATCC #6538), *P. aeruginosa* (ATCC #9027), and *E. coli* (ATCC #8739)), and/or fungi (including plant and tree fungi) (e.g., *Candida albicans, Aspergillus niger* and *Phytophthora ramrum*) on a substrate by applying an antimicrobial, preservative, bactericidal, or fungicidal effective amount of the antimicrobial composition or preservative system of the present invention to the substrate. The antimicrobial composition or preservative system may be applied to the substrate by any method known in the art including, but not limited to, brushing, dipping, soaking, vacuum impregnation, and pressure treatment. A specific embodiment is a method for inhibiting the growth of the tree fungus *Phytophthora ramrum* by applying a fungicidal effective amount of the antimicrobial composition or preservative system of the present invention to the tree fungus or substrate (such as a tree) on which the tree fungus grows. *Phytophthora ramrum* causes Sudden Oak Death.

The antimicrobial composition of the present invention may be prepared by mixing the antimicrobial components, and optionally, solvents, and adjuvants. The mixture may be heated and/or stirred to expedite mixing.

EXAMPLES

The following examples illustrate the invention without limitation. All parts and percentages are given by weight unless otherwise indicated.

Example 1

Each anionic shampoo sample in FIGS. 1-3 were tested as follows. A standardized mixed bacterial solution was prepared according to the following procedure. 3 agar stabs of *S.* aureus (ATCC #6538), *P. aeruginosa* (ATCC #9027), and *E. coli* (ATCC #8739) were separately incubated at about 35 EC for about 24 hours. Each stab was then washed with 3 mL of sterile 0.85% saline solution. The washes of the 3 stabs were pooled together to form an organism mixture. The absorbance of the organism mixture at 530 nm was adjusted to about 1.00 by adding saline. The spectrometer was calibrated with a saline blank. A 5 mL aliquot of the organism mixture was mixed together to produce the standardized mixed bacterial solution. Then, 40 g of each shampoo sample was inoculated with 0.2 mL of the standardized mixed bacterial solution and mixed. 1 g of the mixture was added to a sterile 20×150 mm screw cap test tube.

9 mL of sterile D/E neutralizer broth was added to the test tube and mixed to form a $10^{-1}$ dilution. Serial dilutions were prepared through to a $10^{-6}$ dilution with phosphate buffered water. The serial dilutions were plated onto Tryptic Soy Agar and incubated for 2 days at about 35 EC. Bacteria counts were performed after 21 days.

The anionic protein shampoo composition was comprised of 35% by weight of sodium lauryl ether sulfate; 25% by weight of triethanolamine lauryl sulfate; 3% by weight coconut diethanolamide (cocamide DEA); 1% by weight of hydrolyzed collagen, available as Polypro 5000™ from Hormel Foods of Austin, Minn.; and 36% by weight of deionized water.

The antimicrobial composition containing samples were prepared by mixing the appropriate amounts of the antimicrobial ingredients and the aforementioned anionic protein shampoo composition and heating the mixture to about 50 EC for about 15 minutes.

Figure 2:
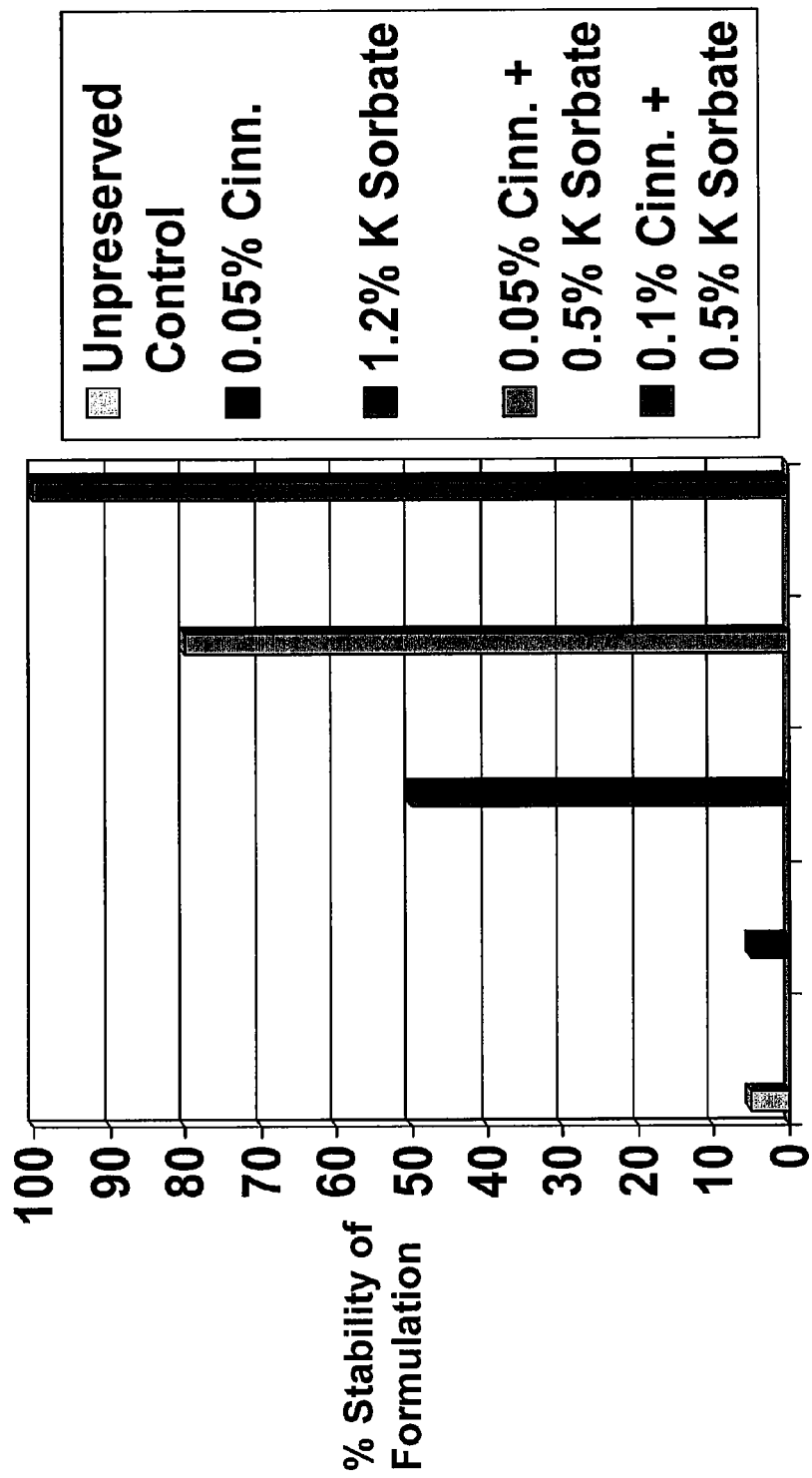
FIG. 2 is a bar graph of the stability of (a) an unpreserved shampoo, (b) a shampoo containing 0.05% (w/w) cinnamaldehyde, (c) a shampoo containing 1.2% (w/w) potassium sorbate, (d) a shampoo containing 0.05% cinnamaldehyde and 0.5% potassium sorbate, and (e) a shampoo containing 0.1% (w/w) cinnamaldehyde and 0.5% (w/w) potassium sorbate after 21 days (based on bacterial count).
Figure 3:
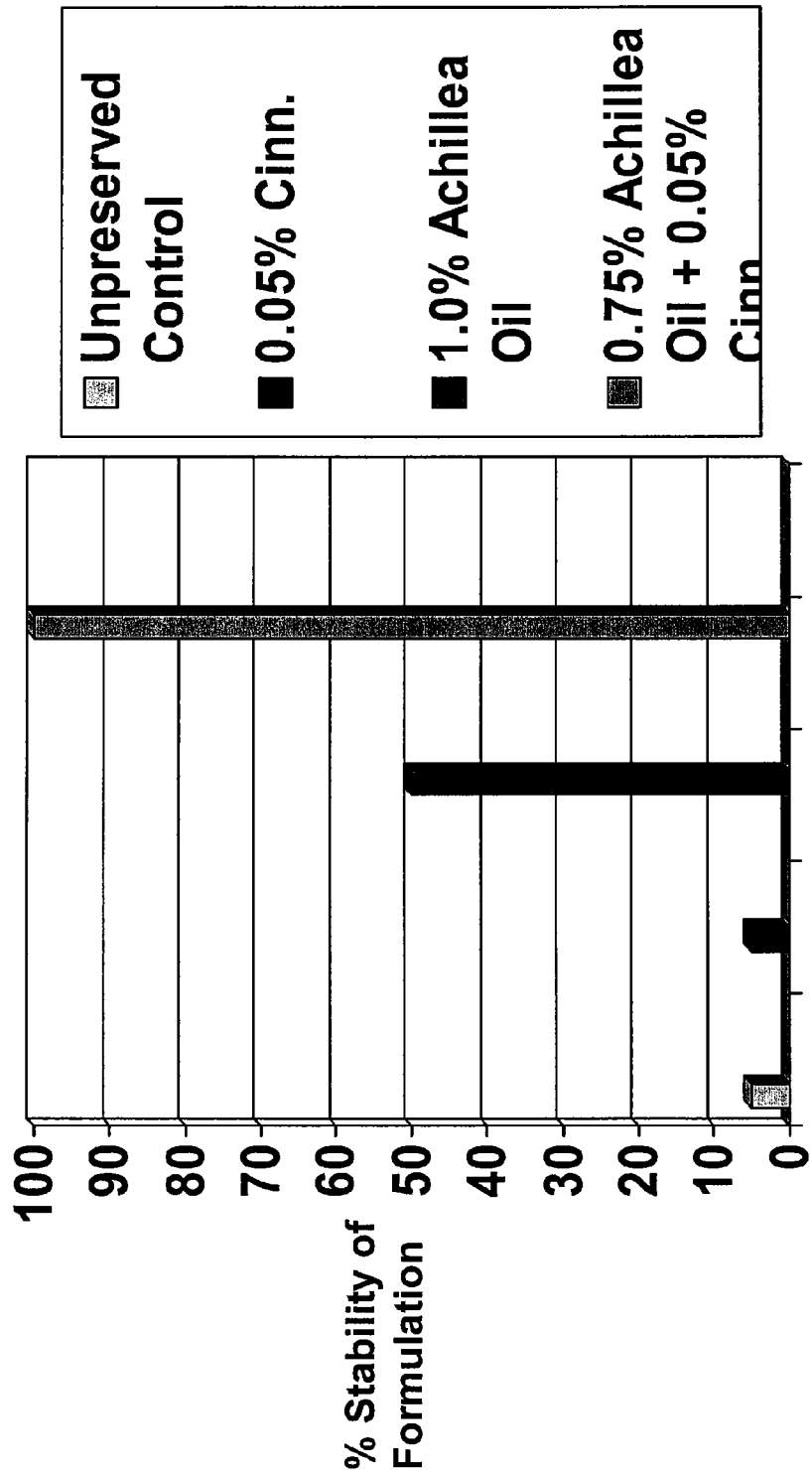
FIG. 3 shows a bar graph of the stability of (a) an unpreserved shampoo, (b) a shampoo containing 0.05% (w/w) cinnamaldehyde, (c) a shampoo containing 1.0% (w/w) achillea oil, and (d) a shampoo containing 0.05% (w/w) cinnamaldehyde and 0.75% (w/w) achillea oil after 21 days (based on bacterial count).
Figure 4:
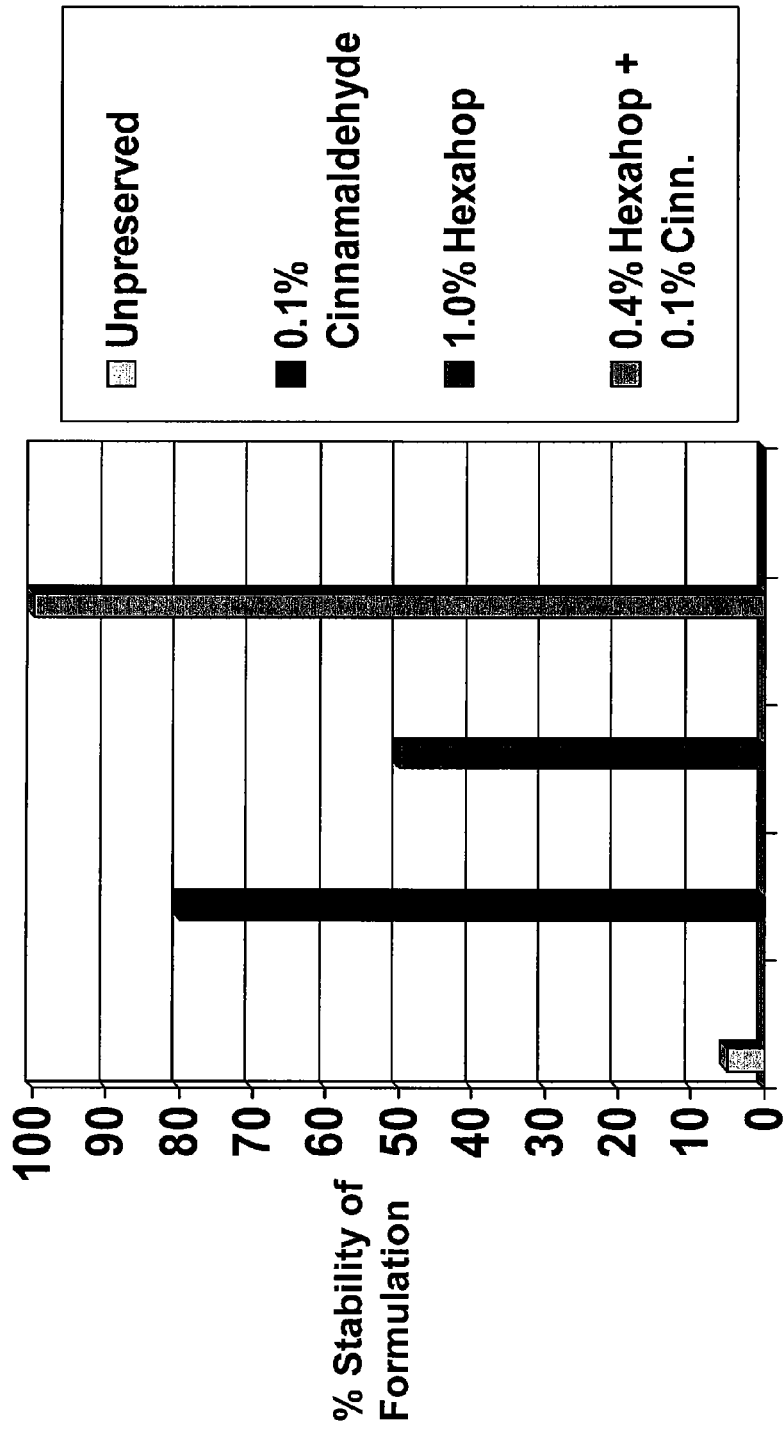
FIG. 4 is a bar graph of the stability of (a) an unpreserved shampoo, (b) a shampoo containing 0.1% (w/w) cinnamaldehyde, (c) a shampoo containing 1.0% (w/w) Hexahop Gold™, and (d) a shampoo containing 0.1% (w/w) cinnamaldehyde and 0.4% (w/w) Hexahop Gold™ after 7 days (based on fungal count).
Figure 5:
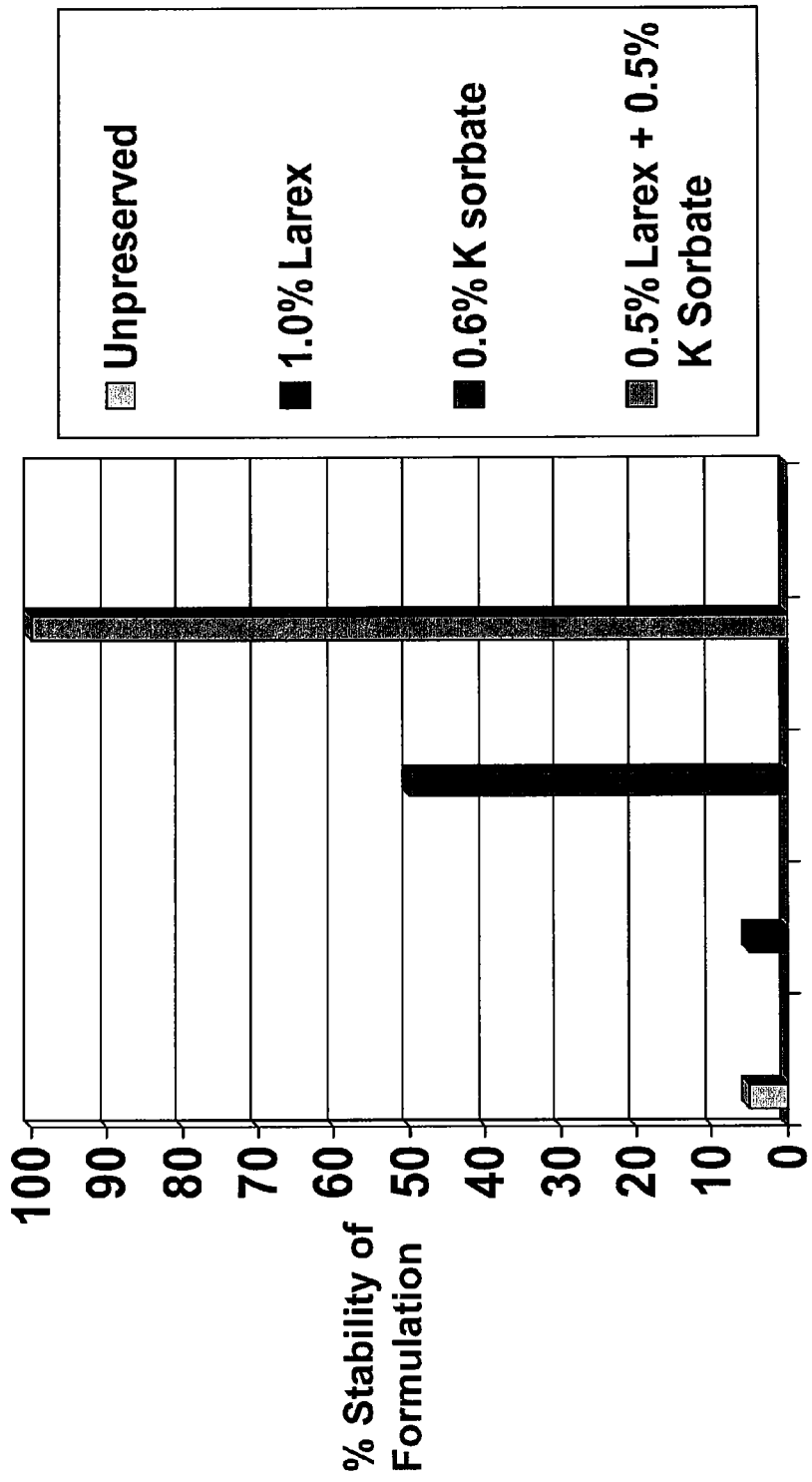
FIG. 5 is a bar graph of the stability of (a) an unpreserved shampoo, (b) a shampoo containing 1.0% (w/w) Larex™ (arabinogalactan), (c) a shampoo containing 0.6% (w/w) potassium sorbate, and (d) a shampoo containing 0.5% (w/w) Larex™ and 0.5% (w/w) potassium sorbate after 14 days (based on fungal count).
Figure 6:
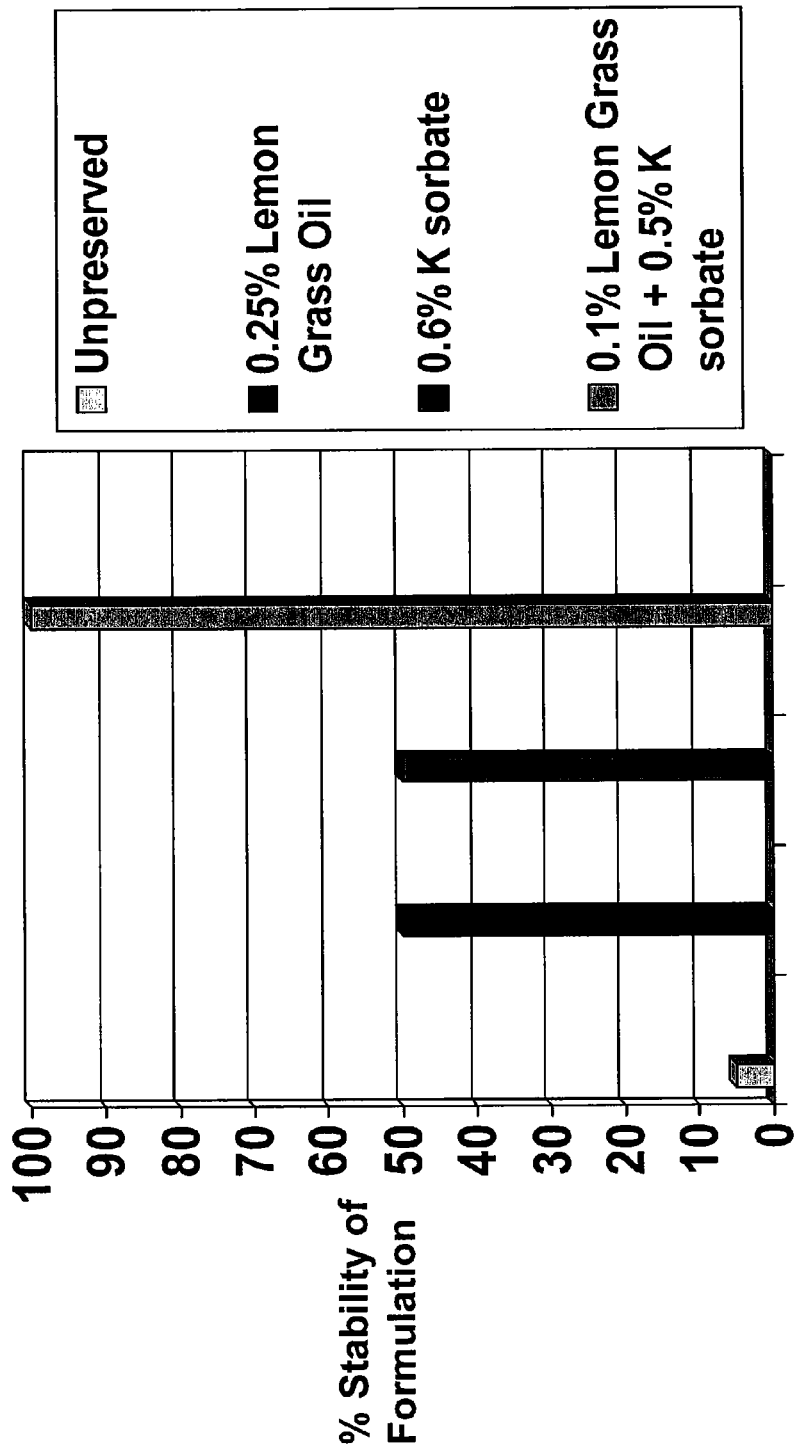
FIG. 6 is a bar graph of the stability of (a) an unpreserved shampoo, (b) a shampoo containing 0.25% (w/w) lemon grass oil, (c) a shampoo containing 0.6% (w/w) potassium sorbate, and (d) a shampoo containing 0.1% (w/w) lemon grass oil and 0.5% (w/w) potassium sorbate after 7 days (based on fungal count).
Figure 7:
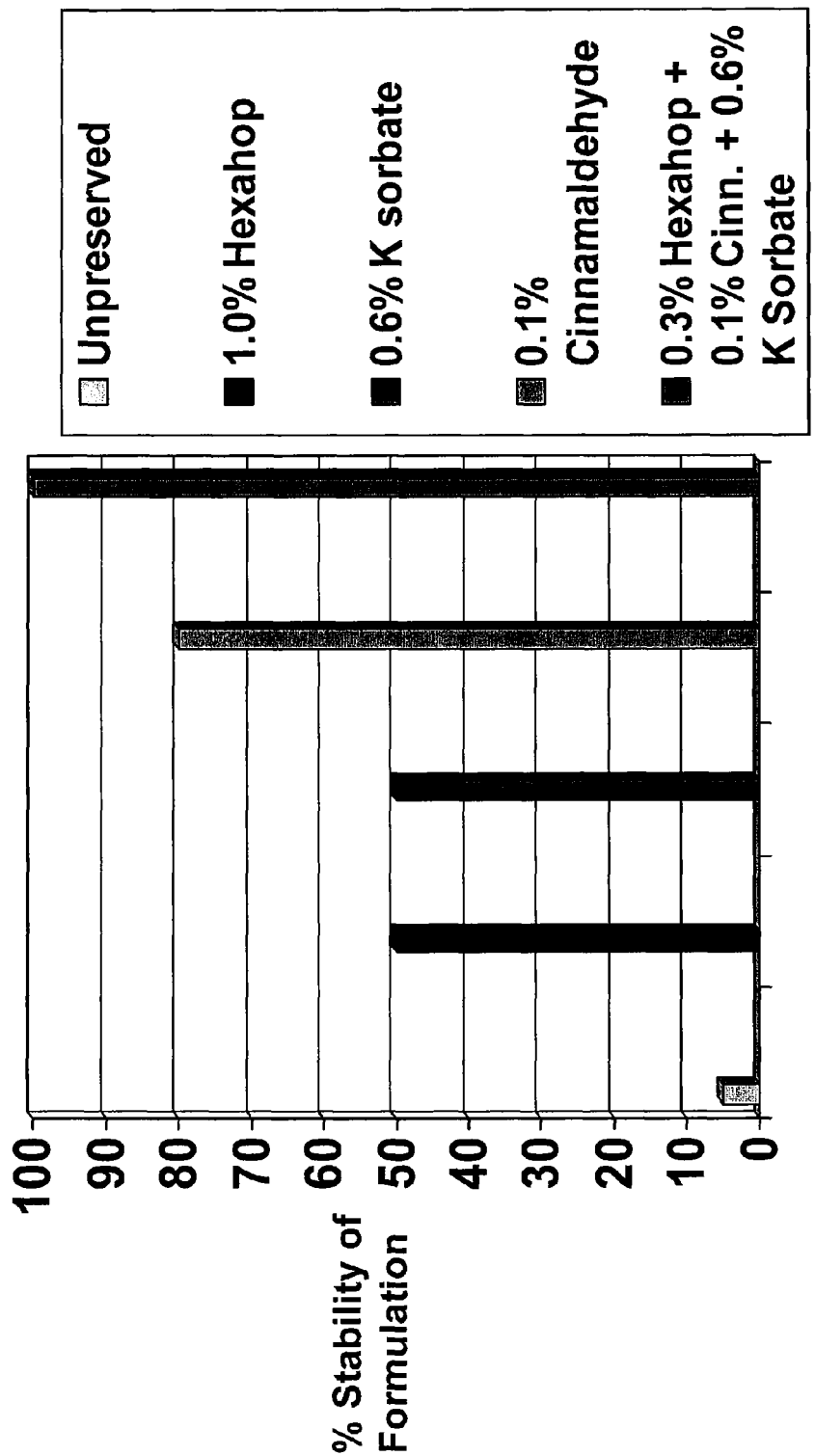
FIG. 7 is a bar graph of the stability of (a) an unpreserved shampoo, (b) a shampoo containing (w/w) Hexahop Gold™, (c) a shampoo containing 0.6% (w/w) potassium sorbate shampoo, (d) a shampoo containing 0.1% (w/w) cinnamaldehyde, and (e) a shampoo containing 0.3% (w/w) Hexahop Gold™, 0.1% (w/w) cinnamaldehyde, and 0.6% (w/w) potassium sorbate after 7 days.

The results are shown in FIGS. 1-3.

Example 2

Each anionic shampoo sample in FIGS. 4-7 were tested as follows. A standard mixed bacterial solution was prepared according to the following procedure. 2 agar slants of *Candida albicans* and 4 agar slants of *Aspergillus niger* were separately incubated at about 25 EC for about 48 hours and 7 days, respectively. Each slant was washed with 3 mL of sterile 0.85% saline solution, collected and macerated in a tissue grinder. Sufficient amounts of 0.85% saline solution were added to each slant to obtain a visual count under a microscope with a Neubauer Hemocytometer of each innoculum of *C. albicans* and *A. niger*. Equal volumes of each standardized innoculum of *C. albicans* and *A. niger* were mixed together to form the standardized mixed fungal solution.

40 g of each shampoo sample was inoculated with 0.4 mL of the standardized mixed fungal solution and mixed. 1 g of the mixture was added to a sterile 20×150 mm screw cap test tube.

9 mL of sterile D/E neutralizer broth was added to the test tube and mixed to form a $10^{-1}$ dilution. Serial dilutions were prepared through to a $10^{-6}$ dilution with phosphate buffered water. The serial dilutions were plated onto Sabourand dextrose agar and incubated 5 days at about 25 EC. Fungal counts were performed after 0, 7, and/or 14 days.

The anionic protein shampoo composition is described in Example 1. The shampoo samples were prepared by mixing the appropriate amounts of the antimicrobial ingredients and the anionic protein shampoo composition and heating the mixture to about 50 EC for about 15 minutes.

The results are shown in FIGS. 4-7.

Example 3

The procedure described in Example 1 was repeated with the preservative formulations set forth in Table 1 below. The pH of the shampoo was adjusted to 6.5. The results are also shown in Table 1.

TABLE 1

| Preservative Formulation | Day 0 cfu/g. | Day 7 cfu/g. | Day 14 cfu/g. | Day 28 cfu/g. |
|---|---|---|---|---|
| 0.3% w/w of a mixture containing 75% potassium sorbate and 25% sodium erythorbate | 1-3 × 10⁶ | <10 | <10 | <10 |
| 0.3% w/w of a mixture containing 75% sodium benzoate and 25% sodium erythorbate | 1-3 × 10⁶ | <10 | <10 | <10 |
| 0.45% w/w sodium erythorbate | 1-3 × 10⁶ | >3 × 10⁶ | >3 × 10⁶ | >3 × 10⁶ |
| 0.45% w/w sodium benzoate | 1-3 × 10⁶ | 1 × 10⁵ | 7 × 10⁵ | <10 |
| 0.45% w/w potassium sorbate | 1-3 × 10⁶ | 1 × 10⁵ | 6 × 10⁴ | N.D. |
| Unpreserved Shampoo | 1-3 × 10⁶ | >3 × 10⁶ | >3 × 10⁶ | >3 × 10⁶ |

From Table 1, synergism for (1) a 0.3% dilution of potassium sorbate (75%) and sodium erythorbate (25%) and (2) a 0.3% dilution of sodium benzoate (75%) and sodium erythorbate (25%) against mixed bacteria in shampoo was calculated by the method described in C. E. Kull et al., "Mixtures of Quaternary Ammonium Compounds and Long-chain Fatty Acids as Antifungal Agents", *Applied Microbiology*, 9:538-541 (1961). The synergism value $(Q_A/Q_a + Q_B/Q_b)$ was determined. $Q_A$ is the concentration of potassium sorbate or sodium benzoate (in percent by weight) in the mixture, which yielded 100% retardation of the bacteria, i.e., resulted in a plate count of <10 cfu/g after 7 days. $Q_a$ is the concentration of potassium sorbate or sodium benzoate alone (in percent by weight) required to yield 100% retardation of the bacteria. $Q_B$ is the concentration of sodium erythorbate (in percent by weight) in the mixture, which yielded 100% retardation of the bacteria. $Q_b$ is the concentration of sodium erythorbate alone (in percent by weight) required to yield 100% retardation of the bacteria.

When the value of $(Q_A/Q_a + Q_B/Q_b)$ is less than one, the mixture is synergistic. Values for $(Q_A/Q_a + Q_B/Q_b)$ of 1 and greater represent an additive effect and an antagonistic effect, respectively. The results are shown in Table 2 below.

TABLE 2

| Preservative Mixture | $Q_A$ | $Q_B$ | $Q_a$ | $Q_b$ | $Q_A/Q_a + Q_B/Q_b$ |
|---|---|---|---|---|---|
| 75% potassium sorbate and 25% sodium erythorbate | 0.225% | 0.075% | 0.45% | 0.45% | 0.67 (<1) |
| 75% Sodium Benzoate and 25% Sodium erythorbate | 0.225% | 0.075% | 0.45% | 0.45% | 0.67 |

Example 4

Each anionic shampoo sample in Table 3 below was tested as follows. A standardized mixed bacterial solution was prepared according to the following procedure. 3 agar stabs of *S. aureus* (ATCC #6538), *P. aeruginosa* (ATCC #9027), and *E. coli* (ATCC #8739) were separately incubated at about 35 EC for about 24 hours. Each stab was then washed with 3 mL of sterile 0.85% saline solution. The washes of the 3 stabs were pooled together to form an organism mixture. The absorbance of the organism mixture at 530 nm was adjusted to about 1.00 by adding saline. The spectrometer was calibrated with a saline blank. A 5 mL aliquot of the organism mixture was mixed together to produce the standardized mixed bacterial solution. Then, 40 g of each shampoo sample was inoculated with 0.2 mL of the standardized mixed bacterial solution and mixed. 1 g of the mixture was added to a sterile 20×150 mm screw cap test tube.

9 mL of sterile D/E neutralizer broth was added to the test tube and mixed to form a $10^{-1}$ dilution. Serial dilutions were prepared through to a $10^{-6}$ dilution with phosphate buffered water. The serial dilutions were plated onto Tryptic Soy Agar and incubated for 2 days at about 35 EC. Bacteria counts were performed after 0, 7, and 14 days. The results are shown in Table 1.

The anionic protein shampoo composition was comprised of 35% by weight of sodium lauryl ether sulfate; 25% by weight of triethanolamine lauryl sulfate; 3% by weight coconut diethanolamide (cocamide DEA); 1% by weight of hydrolyzed collagen, available as Polypro 5000™ from Hormel Foods of Austin, Minn.; and 36% by weight of deionized water.

The cinnamaldehyde and other preservative containing samples were prepared by mixing the appropriate amounts of the preservatives and the aforementioned anionic protein shampoo composition and heating the mixture to about 50 EC for about 15 minutes.

TABLE 3

| Shampoo | *S. aureus*, *P. aeruginosa*, and *E. coli* (cfu/g) | | |
|---|---|---|---|
| | Day 0 | Day 7 | Day 14 |
| Unpreserved Anionic Protein Shampoo Composition | $3.0 \times 10^7$ | $3.0 \times 10^7$ | $3.0 \times 10^7$ |
| 0.25% Cinnamaldehyde | $3.0 \times 10^7$ | <10 | <10 |
| 0.20% Cinnamaldehyde | $3.0 \times 10^7$ | <10 | <10 |
| 0.10% Cinnamaldehyde | $3.0 \times 10^7$ | $1.0 \times 10^1$ | <10 |
| 1.0% Benzyl Alcohol | $3.0 \times 10^7$ | $5.0 \times 10^6$ | $5.3 \times 10^6$ |
| 1.0% LiquaPar Optima* | $3.0 \times 10^7$ | $3.0 \times 10^7$ | $2.0 \times 10^7$ |
| 1% Tea Tree Oil | $3.0 \times 10^7$ | $3.0 \times 10^7$ | $3.0 \times 10^7$ |
| 1% d-Limonene | $3.0 \times 10^7$ | $3.0 \times 10^7$ | $3.0 \times 10^7$ |
| 1% Gerniol | $3.0 \times 10^7$ | $3.0 \times 10^7$ | $3.0 \times 10^7$ |
| 1% Nerol | $3.0 \times 10^7$ | $3.0 \times 10^7$ | $3.0 \times 10^7$ |
| 1% Citral | $3.0 \times 10^7$ | $3.0 \times 10^7$ | $3.0 \times 10^7$ |
| 1% Eugenol | $3.0 \times 10^7$ | $3.0 \times 10^7$ | $3.0 \times 10^7$ |
| 1% Hexahop | $3.0 \times 10^7$ | $3.0 \times 10^7$ | $3.0 \times 10^7$ |

*LiquaPar Optima is phenoxyethanol (and) methylparaben (and) isopropylparaben (and) isobutylparaben (and) butylparaben and is available from ISP Labs of Wayne, NJ.

All percentages in Table 3 are in percent by weight based upon 100% by weight of total shampoo.

Example 5

Each anionic shampoo sample in Table 4 below was tested as follows. A standard mixed bacterial solution was prepared according to the following procedure. 2 agar slants of *Candida albicans* and 4 agar slants of *Aspergillus niger* were separately incubated at about 25 EC for about 48 hours and 7 days, respectively. Each slant was washed with 3 mL of sterile 0.85% saline solution, collected and macerated in a tissue grinder. Sufficient amounts of 0.85% saline solution were added to each slant to obtain a visual count under a microscope with a Neubauer Hemocytometer of each innoculum of *C. albicans* and *A. niger*. Equal volumes of each standardized innoculum of *C. albicans* and *A. niger* were mixed together to form the standardized mixed fungal solution.

40 g of each shampoo sample was inoculated with 0.4 mL of the standardized mixed fungal solution and mixed. 1 g of the mixture was added to a sterile 20×150 mm screw cap test tube.

9 mL of sterile D/E neutralizer broth was added to the test tube and mixed to form a $10^{-1}$ dilution. Serial dilutions were prepared through to a $10^{-6}$ dilution with phosphate buffered water. The serial dilutions were plated onto Sabourand dextrose agar and incubated 5 days at about 25 EC. Fungal counts were performed after 0 and 14 days. The results are shown in Table 9.

The anionic protein shampoo composition is described in Example 4. The shampoo samples were prepared by mixing the appropriate amounts of the preservatives and the anionic protein shampoo composition and heating the mixture to about 50 EC for about 15 minutes.

TABLE 4

| Shampoo | Fungal Plate Count (cfu/g) | | |
|---|---|---|---|
| | Day 0 | Day 7 | Day 14 |
| Unpreserved Anionic Protein Shampoo Composition | $1.0 \times 10^5$ | $4.5 \times 10^4$ | $8.5 \times 10^4$ |
| 0.20 Cinnamaldehyde | $1.0 \times 10^5$ | <10 | <10 |
| 0.10% Cinnamaldehyde | $1.0 \times 10^5$ | $3.0 \times 10^1$ | <10 |
| 0.05% Cinnamaldehyde | $1.0 \times 10^5$ | $8.0 \times 10^3$ | <10 |
| 1.0% Benzyl Alcohol | $1.0 \times 10^5$ | $6.0 \times 10^3$ | $6.0 \times 10^4$ |
| 1.0% LiquaPar Optima | $1.0 \times 10^5$ | $4.0 \times 10^4$ | $3.0 \times 10^4$ |

Example 6

Each cream sample in Table 5 below was tested by the procedure described in Example 1. A glyceryl monostearate (GMS) cream as described in Table 3 below was prepared as follows. The polyoxyethylene glyceryl monostearate, glyceryl monostearate, cetearyl alcohol, and myristyl propionate were mixed and heated to 60 EC in a first container. The glycerin and sterile deionized water were mixed and heated to 60 EC in a second container. The solution in the first container was poured into the second container. The second container was maintained at 60 EC for 10 minutes. The solution in the second container was allowed to cool. The pH of the solution was adjusted to pH 7 with sodium hydroxide to yield the GMS cream.

TABLE 5

| Ingredient Trade Name | Chemical Name | Amount (% w/w) |
|---|---|---|
| Aldosperse[7] MS-20 (Lonza) | Polyoxyethylene (POE) glyceryl monostearate | 4.00 |
| Aldo[7] (Lonza) | Glyceryl monostearate | 6.00 |
| TA 1618 (Proctor & Gamble) | Cetearyl alcohol | 1.50 |
| Lonzest[7] 143-S (Lonza) | Myristyl propionate | 8.00 |
| Glycon[7] G-100 (Lonza) | Glycerin | 5.00 |
| — | Sterile Deionized Water | 75.50 |
| Total | | 100.00 |

The cream samples shown in Table 6 below were prepared by mixing the appropriate amounts of the preservatives and the GMS cream and heating the mixture to 50 EC for 10-15 minutes. The results are shown in Table 6 below.

TABLE 6

| Cream | S. aureus, P. aeruginosa, and E. coli (cfu/g) | | |
|---|---|---|---|
| | Day 0 | Day 7 | Day 14 |
| Unpreserved GMS Cream | $3.0 \times 10^7$ | $3.0 \times 10^7$ | $3.0 \times 10^7$ |
| 0.25% Cinnamaldehyde | $3.0 \times 10^7$ | <10 | <10 |
| 0.10% Cinnamaldehyde | $3.0 \times 10^7$ | $4.0 \times 10^4$ | $9.3 \times 10^5$ |

The cream samples shown in Table 7 below were prepared by mixing the appropriate amounts of the preservatives and the GMS cream and heating the mixture to 50 EC for 10-15 minutes. The results are shown in Table 7 below.

TABLE 7

| Cream | Fungal Plate Count (cfu/g) | | |
|---|---|---|---|
| | Day 0 | Day 7 | Day 14 |
| Unpreserved GMS Cream | $1.0 \times 10^5$ | $2.3 \times 10^5$ | $1.5 \times 10^5$ |
| 0.25% Cinnamaldehyde | $1.0 \times 10^5$ | <10 | <10 |
| 0.10% Cinnamaldehyde | $1.0 \times 10^5$ | <10 | <10 |

Example 7

The procedure in Example 4 was repeated with the shampoo samples shown in Table 8 below. The results are shown in Table 8.

TABLE 8

| Cream | S. aureus, P. aeruginosa, and E. coli (cfu/g) | | |
|---|---|---|---|
| | Day 0 | Day 7 | Day 14 |
| Unpreserved Anionic Protein shampoo Composition | $3.0 \times 10^6$ | $3.0 \times 10^7$ | $3.0 \times 10^7$ |
| 0.10% Cinnamaldehyde | $3.0 \times 10^6$ | $1.0 \times 10^1$ | <10 |
| 0.05% Cinnamaldehyde | $3.0 \times 10^6$ | $6.5 \times 10^6$ | $1.0 \times 10^7$ |
| 0.05% Glydant 2000 ™* | $3.0 \times 10^6$ | $2.0 \times 10^2$ | $1.0 \times 10^2$ |
| 0.02% Glydant 2000 ™ and 0.025% Cinnamaldehyde | $3.0 \times 10^6$ | <10 | <10 |

*Glydant 2000 ™ is a 70% solution of hydantoin species including about 36% dimethylol dimethyl hydantion (DMDMH), about 29% monomethylol dimethylhydantoin (MMDMH), and about 5% dimethyl hydantoin (DMH); and 30% water and is available from Lonza, Inc. of Fair Lawn, NJ.

Synergism for the cinnamaldehyde/Glydant 2000™ solutions in Table 8 against *S. aureus, P. aeruginosa,* and *E. coli* was calculated by the method described in C. E. Kull et al., A Mixtures of Quaternary Ammonium Compounds and Long-chain Fatty Acids as Antifungal Agents@, *Applied Microbiology,* 9:538-541 (1961). The synergism value $(Q_A/Q_a+Q_B/Q_b)$ in Table 7 was determined. $Q_A$ is the concentration of cinnamaldehyde (in percent by weight) in the mixture, which yielded 100% retardation of the bacteria, i.e., resulted in a plate count of <10 cfu/g after 14 days. $Q_a$ is the concentration of cinnamaldehyde alone (in percent by weight) required to yield 100% retardation of the bacteria. $Q_B$ is the concentration of Glydant 2000™ (in percent by weight) in the mixture, which yielded 100% retardation of the bacteria. $Q_b$ is the concentration of Glydant 2000™ alone (in percent by weight) required to yield 100% retardation of the bacteria.

When the value of $(Q_A/Q_a+Q_B/Q_b)$ is less than one, the mixture is synergistic. Values for $(Q_A/Q_a+Q_B/Q_b)$ of 1 and greater than 1, represent an additive effect and an antagonistic effect, respectively.

The results are shown in Tables 9 and 10 below.

TABLE 9

| | For Day 7 | | | | |
|---|---|---|---|---|---|
| Preservative Mixture | $Q_A$ | $Q_B$ | $Q_a$ | $Q_b$ | $Q_A/Q_a + Q_B/Q_b$ |
| 0.05% Glydant 2000 ™ | — | — | 0.05% | — | — |
| 0.10% Cinnamaldehyde | — | — | — | 0.1% | — |
| 0.02% Glydant 2000 ™ and 0.025% Cinnamaldehyde | 0.02% | 0.025% | — | — | 0.65 |

TABLE 10

| | For Day 14 | | | | |
|---|---|---|---|---|---|
| Preservative Mixture | $Q_A$ | $Q_B$ | $Q_a$ | $Q_b$ | $Q_A/Q_a + Q_B/Q_b$ |
| 0.05% Glydant 2000 ™ | — | — | 0.05% | — | — |
| 0.10% Cinnamaldehyde | — | — | — | 0.05% | — |
| 0.02% Glydant 2000 ™ and 0.025% Cinnamaldehyde | 0.02% | 0.025% | — | — | 0.90 |

Example 8

The Minimum Inhibitory Concentration (MIC) of the preservative mixtures was tested. The MIC is the lowest concentration of an ingredient that will inhibit the growth of an organism. This study was conducted using the Hamilton Micro Lab AT Plus Autodilutor Liquid handling System. The programs for the auto-dilutor were based on Lonza's Standard Application Method SAPM#412-01-1. The Hamilton Autodilutor was used to dilute the starting concentrations of the preservative combination by 50% using nutrient broth in 96 well micro titer plates and also to inoculate the microorganism in the test samples.

This preservatives tested were Isocil™ (a blend of methyl isothiazolinone and methyl-chloro-isothiazolinone), Benzocil™ (benzisothiazolinone) and Lonzagard™ (benzethonium chloride), all of which are available from Lonza Inc. of Fair Lawn, N.J., in various concentrations and combinations with cinnamaldehyde. Controls were also included in each test plate. Each preservative combination was tested in duplicate against *Staphylococcus aureus* (ATCC #6538) and *Escherichia coli* (ATCC #8739).

Test plates were diluted by the Hamilton Autodilutor and then inoculated with the test organism to achieve approximately $10^6$ colony forming units/gram in the test sample (cfu/g). The plates were then incubated in a 32 degree Celsius oven for 72 hours. Results were determined by checking for growth in the test samples versus the control wells on each plate (visual determination of turbidity in the wells). The MIC shown below in Table 11 was reported as the lowest test levels of preservative or preservative blend that did not show any growth.

A mixture of 7.5 ppm (active) Benzocil™ and 25 ppm cinnamaldehyde effectively inhibited growth. Also, a mixture of 0.47 ppm (active) Isocil™ and 6.3 ppm cinnamaldehyde effectively inhibited growth.

TABLE 11

| Test Material | MIC for *S. Aureus* |
|---|---|
| Cinnamaldehyde | 125 ppm |
| Isocil ™ (Isothiazolinone) | 0.585 ppm (active) |
| Benzocil ™ (Benzoisothiazolinone) | 9.375 ppm (active) |

Synergism values for the Isocil™/cinnamaldehyde and Benzocil™/cinnamaldehyde combinations were calculated from the MIC values reported in Table 11 by the method described in Kull, supra, referred to above, and are set forth in Tables 12 and 13, below.

TABLE 12

| Preservative Mixture | $Q_A$ | $Q_B$ | $Q_a$ | $Q_b$ | $Q_A/Q_a + Q_B/Q_b$ |
|---|---|---|---|---|---|
| 0.585 ppm (active) Isocil ™ | — | — | 0.585 | — | — |
| 125 ppm Cinnamaldehyde | — | — | — | 125 | — |
| 0.47 ppm (active) Isocil ™ and 6.3 ppm Cinnamaldehyde | 0.47 | 6.3 | — | — | 0.85 |

TABLE 13

| Preservative Mixture | $Q_A$ | $Q_B$ | $Q_a$ | $Q_b$ | $Q_A/Q_a + Q_B/Q_b$ |
|---|---|---|---|---|---|
| 9.375 ppm (active) Benzocil ™ | — | — | >9.375 | — | — |
| 125 ppm Cinnamaldehyde | — | — | — | >125 | — |
| 7.5 ppm (active) Benzocil ™ and 25 ppm Cinnamaldehyde | 7.5 | 25 | — | — | <1.0 |

Example 9

The color stability of the cinnamaldehyde/potassium sorbate mixtures described below were tested with a Gardner color test. Hydrochloric acid was added to adjust the pH of the formulation to the pH specified. The results are shown below

| | Stabilizer | | | | |
|---|---|---|---|---|---|
| | None | | | Hydrochloric Acid | |
| | | Temperature | | | |
| | Initial | Room Temperature | 37° C. | Room Temperature | 37° C. |
| Initial pH | 10.60 | 10.60 | 10.60 | 8.96 | 8.96 |
| Color | 6 | 10-11 | 14-15 | 7-8 | 11-12 |
| Water | 33.9 | 34.2 | 34.1 | 34.0 | 34.4 |
| K sorbate | 41.5 | 42.3 | 42.3 | 44.0 | 43.4 |
| Cinnamaldehyde | 14.8 | 15.1 | 14.9 | 15.5 | 15.6 |
| Final pH | 9.91 | 9.83 | 9.82 | 8.67 | 8.67 |

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

We claim:

1. An antimicrobial composition comprising an antimicrobial effective amount of a mixture consisting essentially of:
    (a) benzoic acid, or a salt thereof; and
    (b) δ-gluconolactone,
    wherein the weight ratio of component (a) to component (b) is from about 0.2:1 to about 5:1.

2. The antimicrobial composition of claim 1, wherein the salt of benzoic acid is sodium benzoate.

3. The antimicrobial composition of claim 1, further comprising a solvent.

4. The antimicrobial composition of claim 3, wherein the solvent is selected from water, glycols, alcohols, and mixtures thereof.

5. The antimicrobial composition of claim 4, wherein the solvent is a mixture of water and a glycol.

6. The antimicrobial composition of claim 5, wherein the glycol is glycerin.

7. The antimicrobial composition of claim 4, wherein the solvent is a mixture of water and an alcohol.

8. The antimicrobial composition of claim 7, wherein the alcohol is ethanol.

9. The antimicrobial composition of claim 1, wherein said antimicrobial effective mixture is present at a concentration of from about 0.01 to about 2% by weight, based on 100% weight of the total composition.

10. A method of killing and/or inhibiting the growth of microorganisms on a substrate comprising applying an effective amount of the antimicrobial composition of claim 1 to the substrate.

11. The method of claim 10, wherein the microorganisms are selected from *S. aureus*, *P. aeruginosa*, *E. coli*, *Candida albicans*, *Aspergillus niger* and *Phytophthora ramrum*.

12. The antimicrobial composition of claim 2, wherein the weight ratio of δ-gluconolactone to sodium benzoate is from about 1:1 to about 5:1.

* * * * *